United States Patent [19]

Shah et al.

[11] Patent Number: 4,469,674
[45] Date of Patent: Sep. 4, 1984

[54] STABLE ORAL COMPOSITIONS CONTAINING ZINC AND FLUORIDE COMPOUNDS

[75] Inventors: Nutan B. Shah, New Rochelle, N.Y.; Nicholas F. Schmidt, Brookfield, Conn.

[73] Assignee: Richardson-Vicks Inc., Wilton, Conn.

[21] Appl. No.: 490,259

[22] Filed: May 2, 1983

Related U.S. Application Data

[63] Continuation-in-part of Ser. No. 299,046, Sep. 3, 1981, abandoned.

[51] Int. Cl.³ ............................ A61K 7/16; A61K 7/18
[52] U.S. Cl. ........................................ 424/52; 424/48; 424/49
[58] Field of Search ...................... 424/48–58, 424/145, 152, 289

[56] References Cited

U.S. PATENT DOCUMENTS

| | | | |
|---|---|---|---|
| 2,527,686 | 10/1950 | Sandberg | 424/52 |
| 2,913,373 | 11/1959 | Weisz et al. | 424/52 |
| 3,282,792 | 11/1966 | Fiscella | 424/52 |
| 3,445,567 | 5/1969 | Muhler | 424/52 |
| 3,888,976 | 6/1975 | Mlkvy et al. | 424/44 |
| 4,022,880 | 5/1977 | Vinson et al. | 424/49 |
| 4,078,053 | 3/1978 | De Paola | 424/52 |
| 4,082,841 | 4/1978 | Pader | 424/52 |
| 4,100,269 | 7/1978 | Pader | 424/49 |
| 4,138,477 | 2/1979 | Gaffar | 424/52 |
| 4,289,754 | 9/1981 | Dhabhar et al. | 424/52 |
| 4,289,755 | 9/1981 | Dhabhar et al. | 424/52 |

*Primary Examiner*—Shep K. Rose

[57] ABSTRACT

An oral composition containing zinc salicylate, zinc lactate or zinc gluconate in combination with an ionic fluoride salt.

20 Claims, No Drawings

STABLE ORAL COMPOSITIONS CONTAINING ZINC AND FLUORIDE COMPOUNDS

CROSS REFERENCE TO RELATED APPLICATION

This is a continuation-in-part application of our copending application Ser. No. 299,046, filed Sept. 3, 1981, now abandoned.

FIELD OF THE INVENTION

This invention relates to stable oral compositions containing zinc and fluoride.

BACKGROUND OF THE INVENTION

The prior art is replete with oral compositions containing zinc salts for various beneficial effects believed to be imparted by the zinc ion, for example, reduction of calculus formation or inhibition of offensive mouth odor due to fermentation and putrefaction occurring in the oral cavity. However, despite the heretofore known use of zinc compounds in dental compositions, their use has not been without certain drawbacks. For example, when such soluble zinc compounds have been employed, it has not been possible to satisfactorily incorporate a soluble ionic fluoride salt, such as an alkali metal, ammonium, stannous and the like fluorides, for anti-caries activity in the compositions due to the inherent chemical incompatibility therebetween in the presence of water. This is generally evidenced by the precipitation of insoluble fluoride with a resultant decrease in the amount of efficacious fluoride ion available in the composition.

In U.S. Pat. No. 2,527,686, for example, a mouthwash is disclosed containing soluble zinc chloride, soluble ionic fluoride and, in addition, formaldehyde and two ferments, papain and malt. However, the zinc/fluoride combination is not stable in such a formulation as evidenced by undesirable cloudiness and precipitation of insoluble by-products.

Attempts have thus been made either to use insoluble or sparingly soluble zinc salts or to utilize zinc which has been chemically modified in some manner, for example, by interaction with other adjuvants in order to decrease its potential for forming an insoluble by-product in the presence of ionic fluoride, such as by complexation with a zinc complexing agent, or by addition of a solvating agent to effect solvation of the zinc salt, or the like. For example, in U.S. Pat. No. 4,138,477, oral compositions are disclosed containing a zinc-polymer complex formed by the reaction of a zinc salt and an anionic polymer; in U.S. Pat. Nos. 4,289,754 and 4,325,939, an alkali metal or ammonium zinc citrate complex is described; and in U.S. Pat. No. 4,289,755, entitled "Stable Mouthwash Compositions Containing Zinc and Fluoride Compounds", the solvation of zinc citrate by the addition of citric acid is described.

Either or both of the zinc and fluoride salts may also be physically modified in order to lessen the problem of zinc/fluoride incompatibility for example, by use of well known sustained release, microencapsulation or the like physical forms which allow permeation of the particular salt from protective particles into the oral composition over a period of time, thereby reducing the rate of undesirable interaction between the two salts. For example, in U.S. Pat. No. 4,220,552, microencapsulation of sodium fluoride by a particular pretreated form of a lower alkyl cellulose is disclosed for use in dental formulations.

It is therefore highly desirable to provide a stable oral composition containing a water soluble zinc salt capable of preventing and controlling mouth odor but which does not present any substantial chemical incompatibility when admixed with an ionic fluoride salt in the presence of water. It is also desirable that said zinc salt and said fluoride salt be utilized as such without the need for either or both being modified by chemical or physical means.

BRIEF DESCRIPTION OF THE INVENTION

In accordance with the invention, a stable oral composition is provided comprising an oral vehicle, a water soluble organic zinc salt and a soluble ionic fluoride salt, said zinc salt and said fluoride salt being essentially unmodified in situ by additional chemical or physical agents.

DETAILED DESCRIPTION OF THE INVENTION

Provided herewith are stable oral formulations comprising a combination of a water soluble organic zinc salt selected from the group consisting of zinc salicylate (preferred), zinc lactate and zinc gluconate, including mixtures thereof, as an effective agent against mouth odor and an inorganic water soluble ionic fluoride salt as a source of fluoride ion in solution for effective anti-caries activity. Typical such ionic fluorides include ammonium fluoride and alkali metal, alkaline earth metal and heavy metal fluoride salts, e.g. sodium fluoride, potassium fluoride, lithium fluoride, stannous fluoride, stannic fluoride, barium fluoride, and the like ionic fluoride salts generally acceptable in oral formulations as a source of soluble fluoride ion Ammonium fluoride, alkali metal and tin fluorides, particularly sodium and stannous fluoride, respectively, and mixtures thereof are preferred Other fluorine-containing compounds such as, for example, those which provide fluorine in bound anionic form, such as, for example, in the following anions: hexafluorosilicates, fluorzirconates, monofluorophosphates, tetrafluoroborates and the like, which fluorine-containing anions are not "ionic fluoride salts" contemplated by this invention as being incompatible with zinc ions in solution, since they do not yield simple fluoride ions.

Surprisingly, no significant incompatibility is observed between the three aforementioned zinc salts and said ionic fluorides in simple solution so that the need heretofore for chemically or physically modifying the zinc and/or fluoride components by additional adjuvants which inhibit the interaction between zinc ion and fluoride ion is eliminated.

Accordingly, the oral compositions of this invention comprise an oral vehicle, an effective amount for controlling mouth odor of a zinc salt selected from the group consisting of zinc salicylate, zinc lactate, zinc gluconate and mixtures thereof and an effective anti-caries amount of a soluble ionic fluoride salt, said zinc salt and said fluoride salt being in situ in essentially free form. As the oral vehicle, any conventional dentifrice may be utilized. The most preferred oral compositions of this invention are liquids, particularly mouthwashes, wherein the problem of zinc/fluoride incompatability has been particularly troublesome heretofore.

In the subject compositions, the preferred amount of zinc salt employed is sufficient to provide from about 0.01 to about 5.0 weight percent of theoretical zinc element, more preferably from about 0.05 to about 2.0 weight percent of elemental zinc, and most preferably from about 0.08 to about 1.0 weight percent of elemental zinc. As used herein, the term "weight percent" denotes either weight/weight (w/w) or weight/volume (w/v) percent, i.e., the weight percent of elemental zinc based on the total weight or total volume (i.e., 100 percent) of the final composition depending on whether it is a solid or liquid, respectively. In the preferred liquid embodiments utilizing zinc salicylate as the preferred zinc salt, for example, the amount of zinc salicylate is preferably from about 0.05 to about 25.0 w/v percent, more preferably from about 0.25 to about 10.0 w/v percent, and most preferably from about 0.4 to about 5.0 w/v percent.

The amount of ionic fluoride salt preferably employed in the subject compositions is an amount sufficient to provide from about 25 to about 15000 parts per million (ppm) of available fluoride ion, more preferably from about 100 to about 3000 ppm of available fluoride ion, and most preferably from about 200 to about 1000 ppm of available fluoride ion, again based on the total weight or volume of the final composition depending on whether it is a solid or liquid, respectively. In the preferred liquid embodiments utilizing sodium fluoride as the preferred ionic fluoride salt, for example, the amount of sodium fluoride is preferably from about 0.005 to about 3.0 w/v percent, more preferably from about 0.02 to about 0.6 w/v percent and most preferably from about 0.04 to about 0.2 w/v percent.

As used herein, the term "oral composition" means a product which in the ordinary course of usage is not intentionally swallowed for purposes of systemic administration of the particular therapeutically active ingredient(s), but is retained in the oral cavity for a time sufficient to contact substantially all of the dental surfaces and/or oral tissues for purposes of local activity. Typical oral compositions for purposes of the present invention are those containing at least an amount of water sufficient to solubilize the zinc and fluoride components. The preferred oral compositions are liquid dentifrices (most preferred) such as mouthwashes, rinses, sprays and the like, whether in the form of a concentrate to be diluted prior to use or in final ready-to-use form, and semi-solid dentifrices such as dental creams, pastes and gels, all of which compositions contain substantial amounts of water, generally far more than enough to maintain the specified amount of said zinc and fluoride salts in solution.

The present invention thus provides, as a preferred embodiment, a water-containing oral composition comprising an effective mouth odor inhibiting amount of an organic zinc salt selected from the group consisting of zinc salicylate, zinc lactate, zinc gluconate and mixtures thereof, an effective anti-caries amount of a water soluble inorganic fluoride salt, said zinc salt and said fluoride salt being in situ essentially unmodified by additional chemical or physical means, and an oral vehicle containing at least sufficient water to solubilize said zinc salt and said fluoride salt.

It is understood, however, that it is within the broader aspect of the invention to include other oral compositions with oral vehicles such as lozenges, chewing gums and the like wherein water may be present during their manufacture but little if any when finished.

In certain sugarless gums, for example, there can be used as the binder ingredient a solution of sorbitol in water containing from about 10% to about 80%, preferably from about 50% to about 75% by weight of the sorbitol in water. In others, there is used a gum acacia-in-water system containing from about 30% to about 60%, preferably from about 45% to about 50%, by weight of gum acacia powder in water. Similarly, lozenge formulations may contain water in aqueous systems during formation of the lozenge mass. Incorporation of the zinc salt and ionic fluoride into such formulations may readily be accomplished without fear of precipitating insoluble fluorides by simply utilizing an appropriately prepared aqueous solution of the zinc and fluoride components. After incorporation, drying of the oral composition, as in the case of lozenges, is then performed to remove all or part of the moisture.

As an additional novel aspect of this invention, therefore, there is provided an aqueous solution which comprises water and, dissolved therein, an effective mouth odor inhibiting amount of a zinc salt selected from the group consisting of zinc salicylate, zinc lactate, zinc gluconate and mixtures thereof, preferably in an amount sufficient to provide from about 0.01 to about 0.05 weight percent of theoretical zinc element and an effective anti-caries amount of a water soluble inorganic ionic fluoride salt, preferably in an amount sufficient to provide from about 25 to about 15000 ppm of fluoride ion, said zinc salt and said fluoride salt being in situ substantially in free form, i.e., essentially unmodified by additional chemical or physical adjuvants. Also provided is a dilute ethanolic solution consisting of water, from about 5 to about 40 percent by weight of ethanol, and said amounts of zinc and fluoride salts, such solution providing a stable mouthwash base to which optional ingredients may be added. As noted previously, it is surprising that the three selected zinc salts and said ionic fluorides are compatible and remain simply in such solutions without being chemically or physically modified by additional adjuvants.

The heretofore mentioned oral formulations are exemplary only. Many additional water-containing oral formulations are described in the prior art and, in carrying out this invention, such formulations can be employed so long as there is at least sufficient water to solubilize both the zinc and fluoride components either in the final product or during the course of their manufacture.

The subject oral compositions are generally prepared in accordance with art-recognized practices. Since, however, the two essential components of this invention are the specified zinc salt and the ionic fluoride, it is obvious that any other ingredient in the oral compositions must not interact with either or both of these two components so as to substantially lessen their therapeutic effectiveness. For example, dental cream abrasives or additives which contain soluble phosphates should be avoided due to the interaction with the zinc and abrasives which contain calcium also should be avoided due to the interaction with fluoride. In general, therefore, any conventional ingredients can be used so long as they are compatible, i.e, do not interfere with the activity of the zinc or fluoride component.

As noted previously, the most preferred oral composition is in the form of a liquid dentifrice. Mouthwashes, rinses, sprays, etc. generally comprise a water or water/alcohol solvent system and optionally other ingredients such as flavor, sweeteners, humectants, etc. The alcohol, up to about 40 percent by weight and generally from about 5 to about 40 percent by weight, helps solubilize the flavoring oils and provides an antibacterial effect although other antibacterial or antiseptic agents can also be incorporated in minor amounts, generally at levels from about 0.01 to about 2.0 percent by weight.

The pH of the liquid compositions of this invention should be from acidic pH 3.0 to neutral pH 7.0, preferably within the range of from about 4.0 to about 6.5, and most preferably from about 4.5 to about 5.5. A pH higher than 7.0 should be avoided since the stability of the composition is thereby affected. If desired, the acidic pH of a particular liquid composition if deemed too low can be adjusted to a higher pH up to 7.0 by addition of suitable alkali, e.g., a dilute solution of ammonium, sodium or potassium hydroxide.

Since the problem of zinc/fluoride incompatibility is obviated by the present invention, the subject compositions can be prepared without undue concern for the order or manner of incorporating the two essential components. For example, the preferred liquid dentifrices can be conveniently prepared by simple addition of ingredients in no particular order to the water or water/alcohol solvent system containing the zinc and fluoride salts, such other optional ingredients being, for example, a humectant such as glycerin, sorbitol, polyethylene glycol and the like to give a moist feel in the mouth, generally up to about 20.0 percent by weight, and preferably from about 5.0 to about 20.0 percent by weight; a natural or synthetic sweetening agent such as dextrose, levulose, saccharin, cyclamate and the like, generally from about 0.05 to about 2.0 percent by weight; a flavoring agent such as peppermint oil, spearmint oil, clove oil, anise oil, orange oil, wintergreen oil (methyl salicylate) and the like, generally from about 0.01 to about 2.0 percent by weight; and a surface-active or sudsing agent such as, for example, a sodium alkylbenzene sulfonate, a sodium alkyl sulfate or a nonionic or anionic organic synthetic detergent, generally from about 0.05 to about 10.0 percent by weight and preferably from about 0.5 to about 5.0 percent by weight, all of which are conventional surfactants utilized in dentifrice formulations. Cationic surface active ingredients are not favored since they may give rise to incompatibility with fluoride ions.

The preferred surfactants are sodium lauryl sulfate, particularly for toothpastes, and the nonionic type of synthetic detergents, particularly for mouthwashes. The nonionic synthetic detergents which can be used herein may be broadly defined as compounds produced by the condensation of a hydrophilic alkylene oxide group with an organic hydrophobic compound which may be aliphatic or alkyl-aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well known class of nonionic synthetic detergents is commercially available under the trade name of "Pluronic". These compounds are formed by condensing ethylene oxide with a hydrophobic base formed by the condensation of propylene oxide with propylene glycol.

Other suitable nonionic synthetic detergents include: the polyethylene oxide condensates of alkyl phenols, those derived from the condensation of ethylene oxide with the product resulting from the reaction of propylene oxide and ethylene diamine, the condensation product of aliphatic alcohols having from 8 to 18 carbon atoms, in either straight chain or branched chain configuration, with ethylene oxide, and the polyoxyethylene derivatives of fatty acid partial esters of sorbitol anhydride and commercially available under the trade name "Tween".

In the substantially solid or semi-solid oral compositions of this invention, such as dental creams, pastes and gels, the liquids and solids should be proportioned to form an extrudable creamy mass of desirable consistency. In general, liquids in these formulations will comprise chiefly water, glycerin, sorbitol, propylene glycol or the like, including suitable mixtures thereof. It is advantageous usually to use a mixture of both water and a humectant or binder such a glycerin or sorbitol, preferably glycerin. The total liquid content will generally be about 20 to 75 percent by weight of the formulation. It is also preferred to use a gelling agent such as a natural or synthetic gum and gumlike material, e.g. Irish moss, gum traganth, xanthan gum, Veegum regular, sodium carboxymethylcellulose, polyvinylpyrrolidone, starch and the like. The Irish moss and sodium carboxymethylcellulose are compatible particularly and are preferred gelling agents. The gum content is usually in an amount up to about 10 percent and preferably about 0.5 to 5 percent by weight of the formulation.

An essential ingredient in dental cream formulations is an effective abrasive amount of a suitable dental abrasive, generally from about 10 to about 60 percent by weight and preferably from about 20 to about 50 percent by weight. As noted previously, this abrasive must not interact with either the zinc or fluoride component. Typical compatible abrasives include, for example, insoluble metaphosphates, finely divided silicas, bentonite and the like. The preferred abrasive is silica.

Various other materials may be incorporated as adjuvants in dental creams. Examples thereof are coloring or whitening agents, preservatives, silicones, chlorophyll compounds, ammoniated materials such as urea, diammoniumphosphate and mixtures thereof, and other constituents. A small amount of colloidal silica, for example, is often incorporated into toothpaste formulations as a thickener, giving some body to the formulation upon swelling when in contact with water. The foregoing adjuvants are suitably selected and incorporated in the instant compositions in amounts which do not substantially adversely affect the properties and characteristics desired for the particular type of composition.

For some purposes it may be desirable to include antibacterial agents in the dental creams. Typical antibacterial agents which may be used in amounts of about 0.01 percent to about 5 percent, preferably about 0.05 percent to about 1.0 percent, by weight of the composition include: $N^1$-(4-chlorobenzyl)-$N^5$-(2,4-dichlorobenzyl)biguanide, p-chlorophenyl biguanide, 4-chlorobenzyhydryl biguanide, 4-chlorobenzhydrylguanylurea, N-3-lauroxpropyl-$N^5$- p-chlorobenzylbeguanide, 1,6-di-p-chlorophenylbiguanidohexane, 1-(lauryldimethylammonium)-8-(p-chlorobenzyldimethlyammonium)octane dichloride, 5,6-dichloro-2-guanidinobenzimidazole, $N^1$-p-chlorophenyl-$N^5$-laurylbiguanide, 5-amino-1,3-bis(2-ethylenyl)-5-methylhexahydropyrimidine, and their non-toxic acid addition salts.

Tooth desensitization agents such as, for example, a nitrate of potassium, lithium or sodium disclosed in U.S. Pat. No. 3,863,006 issued Jan. 28, 1975 to Milton Hodosh, may also be incorporated in tooth desensitizing amounts, generally up to about 20% and preferably about 5% by weight.

Any suitable flavoring or sweetening materials may also be employed. Examples of suitable flavoring constituents include the flavoring oils, e.g. oils of spearmint, peppermint, wintergreen, sassafras, clove, sage, eucalyptus, marjoram, cinnamon, lemon and orange, as well as sodium methylsalicylate. Suitable natural and synthetic sweetening agents include sucrose, lactose, maltose, sorbitol, sodium cyclamate, ammonium glycyrrhizinate and its derivatives and saccharin. Suitably, flavor and sweetening agents may together comprise from about 0.01 to 5 percent or more by weight of the dental cream.

The dental cream should have a pH practicable for use. An acidic to neutral pH from about 3.0 to about 7.0 is preferred with 4.0 to 6.5 most preferred. An appropriate acidic buffer may be used to stabilize the pH, for example, an acid/salt buffer such as citric acid/citrate, malic acid/malate, adipic acid/adipate and the like. Particularly useful when zinc salicylate is employed as the zinc salt component is a buffer of salicylic acid/sodium salicylate. The pH determination is made on a 10% aqueous suspension of the dentifrice. If necessary, conventional acidic materials may be added to adjust the pH as desired.

When visually clear gels are employed, polishing agents comprising alkali metal aluminosilicate complexes are particularly useful, since they have refractive indices close to the refractive indices of gelling agent-liquid (including water and/or humectant) systems commonly used in dentifrices. In clear gels where the refractive index is an important consideration, about 3-30% by weight of water, 0 to about 80% by weight of glycerin, and about 20-80% by weight of sorbitol is preferably employed. A gelling agent, such as a natural or synthetic gum or gum-like material, typically Irish moss, sodium carboxymethylcellulose, methyl cellulose, hydroxyethylcellulose, gum tragacanth, polyvinylpyrrolidone, starch, or preferably hydroxypropyl methyl cellulose or the Carbopols (e.g. 934, 940 and 941) or the like is usually present in toothpastes in an amount up to about 10% by weight, preferably in the range of from about 0.5 to about 5%.

In a toothpaste or gel, the liquids and solids are proportioned to form a creamy or gelled mass which is extrudable from a pressurized container or from a collapsible, e.g. aluminum or lead, tube.

As noted previously, aqueous solutions of the zinc and fluoride components may be utilized in formulating other oral compositions wherein little or no moisture is present in the final product. For example, a chewing gum suitable for use as an oral vehicle herein comprises a gum base and flavoring materials such as those mentioned above for dentifrices. The flavoring materials are present at a level of 0.01% to about 2.0% of the final chewing gum composition. The gum base is a chewable plastic gum material such as natural rubber, chicle, polyvinyl acetate, ester gum, coumarone resin, and paraffin wax. The gum base is typically made from a mixture of two or more plastic gum materials to achieve a preferred degree of plasticity for chewing. Corn syrup is generally added as a softener and binder for the chewing gum and sugar is optionally added as a filler and sweetener. A typical chewing gum suitable as a carrier herein comprises 15% to 30% gum base, 15% to 20% corn syrup, 50% to 65% sugar, and 0.05% to 1.5% flavoring materials. An aqueous solution of the zinc and fluoride components may be incorporated into the corn syrup prior to admixture with the gum base.

Lozenges suitable as carriers herein comprise a hard sugar candy base and one or more flavoring materials. The flavoring materials are present at levels between 0.01 to 2.0%. Optionally, lozenges can contain various other materials. A typical lozenge suitable as an oral vehicle in this invention is a hard candy comprised of a hard candy base containing 0.05% to 1.5% flavor. The hard candy base is a solidified solution of amorphous sugar which is generally formed from a sugar solution which has been cooked at high temperature so as to remove nearly all of the moisture. The flavoring materials and the aqueous zinc/fluoride solution are added before the moisture is removed. The flavoring materials mentioned hereinbefore for dentifrices are also exemplary of those suitable for use in lozenges.

Mouth odor has been attributed to the presence of volatile sulfur compounds (VSC) such as hydrogen sulfide, methyl mercaptan and dimethyl sulfide resulting from putrefactive processes, occuring in the oral cavity. An instrumental gas chromatography (GC) - flame photometric detector (FPD) system is available to detect and measure sub-nanogram VSC levels in mouth air (see J. Tonzetich: Archs oral Biol., Vol. 16, pp. 587-597, 1971; and Intl. Dental J., Vol. 28, No. 3, pp. 309-319, 1978).

Utilizing such methodology, particularly effective results in terms of VSC (mouth odor) inhibition are obtained with the present oral compositions. For example, the mouthwash of Example 1, which constitutes the best mode to date of the present invention, practically eliminates the VSC level immediately after usage and then maintains the VSC level far below the 50% level more than 3 hours later. Three adults each gargled once for 60 seconds with 10 ml of the mouthwash, the maximum amount under recommended OTC guidelines for a fluoride-containing mouthwash. Each subject refrained from eating, drinking, smoking and oral hygiene the night before and on the day of the test. No mouth rinsing with water or other fluid after gargling was permitted in order to maximize product efficacy. At specified time intervals, the mouth air sample (5 ml) was analyzed by the aforementioned methodology for the anti-VSC effect due to the mouthwash. The results obtained are shown in Table 1.

TABLE 1.

| | Anti-VSC Effects Observed From Mouthwash of Example 1 | | |
|---|---|---|---|
| | Time (mins.) | S-ng/5 ml* | % Protection |
| Subject A | Initial | 5.82 | — |
| | 60 | 1.0 | 100 |
| | 120 | 0.0 | 100 |
| | 180 | 0.55 | 90.5 |
| | 240 | 1.97 | 33.3 |
| Subject B | Initial | .25 | — |
| | 60 | 1.0 | 100 |
| | 120 | 1.0 | 100 |
| | 180 | — | — |
| | 210 | 0.5 | 60.0 |
| Subject C | Initial | 1.62 | — |
| | 60 | 1.36 | 17 |
| | 120 | .12 | 57.2 |
| | 180 | .02 | 61.0 |

*"S-ng/5 ml"denotes the measurable amount of sulfur (S) in a 5 ml sample of mouth air measured in nanograms ($10^{-9}$).

The following examples are further illustrative of the present invention, but it is to be understood that the invention is not limited thereto. All percents or parts in the examples are by weight unless otherwise specified.

EXAMPLE 1 - MOUTHWASH

| Component | Amount |
|---|---|
| Zinc salicylate | 5.52 g |
| Sodium fluoride | 0.5 g |
| Alcohol U.S.P. | 52.6 ml |
| Glycerin | 20.0 g |
| Pluronic F-127 | 10.0 g |
| Cinnamaldehyde | 0.9 ml |
| Tween 80 | 1.0 g |
| Saccharin insoluble | 0.5 g |
| Menthol-L—natural | 0.38 g |
| Clove oil | 0.14 ml |
| Color (FD & C Red 40 + D & C Red 33) | 0.003 g |
| Distilled water, to make | 1000.0 ml |

The Pluronic F-127, Tween 80, saccharin, menthol, cinnamaldehyde and clove oil are dissolved in the alcohol. The zinc salicylate is dissolved in about 750 ml distilled water with vigorous stirring (magnetic stirrer) and the sodium fluoride added followed by the glycerin and color. To this aqueous solution is added the alcoholic solution and the final product made to volume with distilled water. The mouthwash (pH=4.68) is clear and stable and no visible precipitation occurs over normal shelf-life. Substitution of an equivalent amount of zinc DL-lactate, zinc D-lactate or zinc gluconate for zinc salicylate in the above formulation also provides stable zinc/fluoride mouthwashes.

EXAMPLE 2 - TOOTHPASTE

| Component | Amount |
|---|---|
| Zinc lactate | 3.0 |
| Stannous fluoride | 0.8 |
| Xanthan gum | 0.55 |
| Glycerin | 8.0 |
| Sorbitol solution (70% w/w) | 42.0 |
| Silica | 32.0 |
| Sodium saccharin | 0.45 |
| Sodium benzoate | 0.1 |
| Sodium lauryl sulfate | 2.0 |
| Colloidal silica | 1.0 |
| Flavor | 1.5 |
| Color (FD & C Blue #1) | 0.003 |
| Distilled water, to make | 100.00 |

The xanthan gum and sodium saccharin are mixed and dispersed in the glycerin. The sorbitol is mixed with about an equal volume of water and the glycerin mixture added to it. The silica, sodium lauryl sulfate and colloidal silica are mixed in at high speed under vacuum and the flavoring and color added. The zinc lactate and stannous fluoride are dissolved in the remaining water (heated slightly). The aqueous solution is stable and clear with no precipitation of insolubles. The sodium benzoate is added to the aqueous solution and the latter admixed with the glycerin mixture. The formulation provides a theoretical value of about 0.8 percent by weight of zinc element and about 2000 ppm of soluble fluoride.

EXAMPLE 3 - CHEWING GUM

| Component | Weight % |
|---|---|
| Zinc gluconate | 0.50 |
| Stannous fluoride | 0.10 |
| Distilled water | 2.50 |
| Gum base | 26.00 |
| Sucrose | 52.00 |
| Corn syrup | 17.00 |
| Flavor | 1.90 |

The zinc and fluoride salts are dissolved in the water (heated slightly) and the aqueous solution admixed with the corn syrup prior to incorporation with the other components.

EXAMPLE 4 - LOZENGE

| Component | Weight % |
|---|---|
| Zinc salicylate | 0.50 |
| Ammonium fluoride | 0.10 |
| Sugar | 80.00 |
| Corn syrup | 11.00 |
| Flavor oil | 0.65 |
| Color | 0.25 |
| Tragacanth mucilage | 5.00 |
| Distilled water | 2.00 |

The zinc and fluoride salts are dissolved in the water (heated slightly) and the aqueous solution admixed with the corn syrup prior to incorporation with the other ingredients into a tenacious lozenge mass with sufficient plasticity for molding and cutting into desired shapes and sizes prior to drying.

EXAMPLE 5 - MOUTHWASH

| Component | % w/w |
|---|---|
| Zinc gluconate | 3.0 |
| Sodium fluoride | 0.5 |
| Alcohol U.S.P. | 15.0 |
| Glycerin | 10.0 |
| Flavor | 0.2 |
| Saccharin | 0.03 |
| FD&C Color | 0.3 |
| Distilled water, to make | 100 ml |

The zinc gluconate, sodium fluoride and alcohol are dissolved in about 50 ml water. The other ingredients are then added to this ethanolic solution.

We claim:

1. A stable water-containing oral composition substantially free of insoluble fluoride precipitants consisting essentially of an effective mouth odor inhibiting amount of an organic zinc salt selected from the group consisting of zinc salicylate, zinc lactate, zinc gluconate and mixtures thereof and an effective anti-caries amount of a water soluble inorganic ionic fluoride salt, said zinc and said fluoride salts being in simple solution without additional adjuvant to inhibit interaction between zinc ion and fluoride ion in an oral vehicle containing at least sufficient water to solubilize said salts.

2. A stable water-containing oral composition substantially free of insoluble fluoride precipitants consisting essentially of an effective mouth odor inhibiting amount of an organic zinc salt selected from the group consisting of zinc salicylate, zinc lactate, zinc gluconate and mixtures thereof and an effective anti-caries amount of a water soluble inorganic ionic fluoride salt selected from the group consisting of ammonium fluoride, alkali metal fluoride, tin fluoride and mixtures thereof, said zinc and said fluoride salts being in simple solution without additional adjuvant to inhibit interaction between zinc ion and fluoride ion in an oral vehicle containing at least sufficient water to solubilize said salts.

3. The composition of claim 2 wherein said composition is a mouthwash.

4. The composition of claim 2 wherein said composition is a toothpaste.

5. The composition of claim 2 wherein said zinc salt is zinc salicylate.

6. The composition of claim 2 wherein said fluoride salt is sodium fluoride.

7. A stable aqueous solution substantially free of insoluble fluoride precipitants consisting essentially of water and, dissolved therein in simple solution without additional adjuvant to inhibit interaction between zinc ion and fluoride ion, an effective mouth odor inhibiting amount of an organic zinc salt selected from the group consisting of zinc salicylate, zinc lactate, zinc gluconate and mixtures thereof and an effective anti-caries amount of a water soluble inorganic fluoride salt selected from the group consisting of ammonium fluoride, alkali metal fluoride, tin fluoride and mixtures thereof.

8. The aqueous solution of claim 7 wherein said zinc salt is zinc salicylate and said fluoride salt is sodium fluoride.

9. A stable aqueous ethanolic solution substantially free of insoluble fluoride precipitants consisting essentially of an aqueous solution of ethanol and, dissolved therein in simple solution without additional adjuvant to inhibit interaction between zinc ion and fluoride ion, an effective mouth odor inhibiting amount of an organic zinc salt selected from the group consisting of zinc salicylate, zinc lactate, zinc gluconate and mixtures thereof and an effective anti-caries amount of a water soluble inorganic fluoride salt selected from the group consisting of ammonium fluoride, alkali metal fluoride, tin fluoride and mixtures thereof.

10. The aqueous ethanolic solution of claim 9 containing from about 5 to about 40 percent by weight of ethanol in water.

11. The aqueous ethanolic solution of claim 9 wherein said zinc salt is zinc salicylate and said fluoride salt is sodium fluoride.

12. A stable aqueous mouthwash solution substantially free of insoluble fluoride precipitants consisting essentially of water and, dissolved therein in simple solution without additional adjuvant to inhibit interaction between zinc ion and fluoride ion, a sufficient amount of an organic zinc salt selected from the group consisting of zinc salicylate, zinc lactate, zinc gluconate and mixtures thereof to provide from about 0.01 to about 5.0 weight percent of theoretical elemental zinc and a sufficient amount of a water soluble inorganic ionic fluoride salt selected from the group consisting of ammonium fluoride, alkali metal fluoride, tin fluoride and mixtures thereof to provide from about 25 to about 15000 parts per million of available fluoride ion.

13. The mouthwash solution of claim 12 wherein said zinc salt provides from about 0.05 to about 2.0 weight percent of theoretical elemental zinc and said fluoride salt provides from about 100 to about 3000 parts per million of available fluoride ion.

14. The mouthwash solution of claim 12 wherein said zinc salt provides from about 0.08 to about 1.0 weight percent of theoretical elemental zinc and said fluoride salt provides from about 200 to about 1000 parts per million of available fluoride ion.

15. The mouthwash solution of claim 14 wherein said zinc salt is zinc salicylate and said fluoride salt is sodium fluoride.

16. A stable aqueous ethanolic mouthwash solution substantially free of insoluble fluoride precipitants consisting essentially of from about 5 to about 40 percent by weight of ethanol in water and, dissolved therein in simple solution without additional adjuvant to inhibit interaction between zinc ion and fluoride ion, a sufficient amount of an organic zinc salt selected from the group consisting of zinc salicylate, zinc lactate, zinc gluconate and mixtures thereof to provide from about 0.01 to about 5.0 weight percent of theoretical elemental zinc and a sufficient amount of a water soluble inorganic ionic fluoride salt selected from the group consisting of ammonium fluoride, alkali metal fluoride salt, tin fluoride, and mixtures thereof to provide from about 25 to about 15000 parts per million of available fluoride ion.

17. The mouthwash solution of claim 16 wherein said zinc salt provides from about 0.05 to about 2.0 weight percent of theoretical elemental zinc and said fluoride salt provides from about 100 to about 3000 parts per million of available fluoride ion.

18. The mouthwash solution of claim 16 wherein said zinc salt provides from about 0.08 to about 1.0 weight percent of theoretical elemental zinc and said fluoride salt provides from about 200 to about 1000 parts per million of available fluoride ion.

19. The mouthwash solution of claim 18 wherein said zinc salt is zinc salicylate and said fluoride salt is sodium fluoride.

20. A mouthwash composition consisting of the following formulation or equivalent thereof:

| | |
|---|---|
| Zinc salicylate | 5.52 g |
| Sodium fluoride | 0.5 g |
| Alcohol U.S.P. | 52.6 ml |
| Glycerin | 20.0 g |
| Pluronic F-127 | 10.0 g |
| Cinnamaldehyde | 0.9 ml |
| Tween 80 | 1.0 g |
| Saccharin insoluble | 0.5 g |
| Menthol-L—natural | 0.38 g |
| Clove oil | 0.14 g |
| Colorant | 0.003 g |
| Distilled water, to make | 1000.00 ml |

* * * * *